(12) United States Patent  
Holmes et al.

(10) Patent No.: US 6,716,218 B2
(45) Date of Patent: Apr. 6, 2004

(54) INSTRUMENT FOR BONE DISTRACTION AND COMPRESSION HAVING RATCHETING TIPS

(75) Inventors: Russell P. Holmes, Boston, MA (US); James F. Marino, LaJolla, CA (US)

(73) Assignee: Hol-Med Corporation, South Easton, MA (US)

( * ) Notice: Subject to any disclaimer, the term of this patent is extended or adjusted under 35 U.S.C. 154(b) by 0 days.

(21) Appl. No.: 10/083,829

(22) Filed: Feb. 27, 2002

(65) Prior Publication Data

US 2002/0123754 A1 Sep. 5, 2002

Related U.S. Application Data

(60) Provisional application No. 60/272,217, filed on Feb. 28, 2001.

(51) Int. Cl.[7] .............................................. A61B 17/58
(52) U.S. Cl. ..................................................... 606/105
(58) Field of Search .......................... 606/90, 105, 99, 606/86, 206, 207, 210; 600/210, 213, 217, 226

(56) References Cited

U.S. PATENT DOCUMENTS

| | | | | |
|---|---|---|---|---|
| 2,002,021 A | * | 5/1935 | Rouse | ........................ 606/105 |
| 2,109,147 A | * | 2/1938 | Grosso | ........................ 606/205 |
| 3,510,923 A | * | 5/1970 | Blake | ........................ 606/158 |
| 3,750,652 A | * | 8/1973 | Sherwin | ........................ 606/90 |
| 3,960,147 A | * | 6/1976 | Murray | ........................ 606/75 |
| 4,896,661 A | * | 1/1990 | Bogert et al. | ................. 606/86 |
| 4,898,161 A | * | 2/1990 | Grundei | ....................... 606/105 |
| 5,122,130 A | * | 6/1992 | Keller | ........................ 606/61 |
| 5,201,734 A | | 4/1993 | Cozad et al. | |
| 5,281,223 A | * | 1/1994 | Ray | ........................ 606/61 |
| 5,529,571 A | * | 6/1996 | Daniel | ........................ 600/219 |
| 5,800,438 A | * | 9/1998 | Tuke et al. | .................... 606/90 |
| 6,165,186 A | | 12/2000 | Fogarty et al. | |

* cited by examiner

Primary Examiner—Eduardo C. Robert
(74) Attorney, Agent, or Firm—Cesari and McKenna, LLP

(57) ABSTRACT

An instrument for bone distraction and compression is provided which has been fitted with ratcheting tips that are rotatably mounted at the working end of a bone distractor. The ratcheting tips are mounted such that they are adjustable to customize the instrument for a particular surgical procedure. The tips may be used to push implants along the rod. The tips can include U-shaped ends that slide around the rod hooks or other components to urge the two to desired positions. It is preferred that the members of the handle are coupled such that when opened, the working ends of the instrument remain parallel to one another.

11 Claims, 4 Drawing Sheets

INSTRUMENT FOR BONE DISTRACTION AND COMPRESSION HAVING RATCHETING TIPS

CROSS-REFERENCE TO RELATED APPLICATION

The present application claims the benefit of U.S. Provisional Patent Application Ser. No. 60/272,217, which was filed on Feb. 28, 2001, by Russell P. Holmes et al. for an INSTRUMENT FOR BONE DISTRACTION AND COMPRESSION HAVING RATCHETING TIPS, and is hereby incorporated by reference.

BACKGROUND OF THE INVENTION

1. Field of the Invention

This invention relates generally to surgical instrumentation and, more specifically, to distractor and compressor instruments.

2. Background Information

Various medical instruments and appliances are used in the treatment of spinal column deformities and injuries. In certain medical circumstances, it is necessary to place is a mechanical device, such as a stabilization rod, adjacent to the spine. This is to promote the natural healing of the spine in a straight spatial disposition, or to enhance straightening of the spine in cases of disease such as scoliosis. In some surgical procedures, chips of bone which have been removed from another portion of the body, such as the hip, are placed in proximity to the healing spinal site. These chips act as mortar to promote bone fusion.

The spinal rods are placed along the spinal column and various fixation appliances are mounted along the rods to maintain the rods in the desired position and orientation. Implants are pushed up and down the rods such as hooks. Rod holders may be used as a stop. While a surgeon is mounting the rods, rod hooks and various other components, the surgeon pushes items along the rod and may either distract bone by pulling it away from the work site or must compress bone to pull it together if broken, for example. A standard distractor/compressor is used to accomplish these and many other actions during spinal surgery.

In certain procedures, the surgeon approaches the spinal column of the patient from an anterior position (the stomach area). Pressure is thus applied from some distance in order to move implants along a rod or to distract or compress a rod in place or to distract bone or implants into the most favorable position. The positioning is important in order to fix the correct position of the rods and the implants while providing the surgeon the best visualization of the work site.

Prior instruments required the surgeon or a member of the surgical team to hold a distractor directly at the desired angle, however, the distractor instrument itself may, in is such a case obstruct the surgeon's view of the work site. It has been know to provide an instrument with a bend in it, to allow a better view, but the bend may not allow the most leverage when a good deal of force is required. Detachable tips have also been used, which detachable tips are placed on the end of a standard distractor allowing distraction or compression at a particular angle which allows the instrument to be rotated out of the surgeon's view yet still applying pressure at the correct position on the rod or bone. However, these detachable tips require either a selection of the appropriate instrument prior to surgery, or may require changing the tips during surgery should the appropriate detachable tip not have been chosen. Additional detachable tips can be expensive and may lead to duplicative instrumentation. Changing tips can cause usage of time and efforts during surgical procedures.

SUMMARY OF THE INVENTION

This invention is an instrument for bone distraction and compression which has been fitted with ratcheting tips which are rotatably mounted at the working end of a bone distractor. The ratcheting tips are mounted such that they are adjustable to customize the instrument for a particular surgical procedure. The tips may be used to push implants along a rod. In that application, the tips include U-shaped ends that slide around the rod hooks or other components to urge the component into the position desired by the surgeon. The ratcheting tips, in accordance with one aspect of the invention, are adjustable at 15° interval positions around a central axis to a maximum of about 90°. It is preferred to provide a ratcheted tip to avoid motion during surgery. The ratcheted tip allows the surgeon to adjust the angle to allow the best visualization, while maintaining the instrument in a plane that allows the optimum force to be applied.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
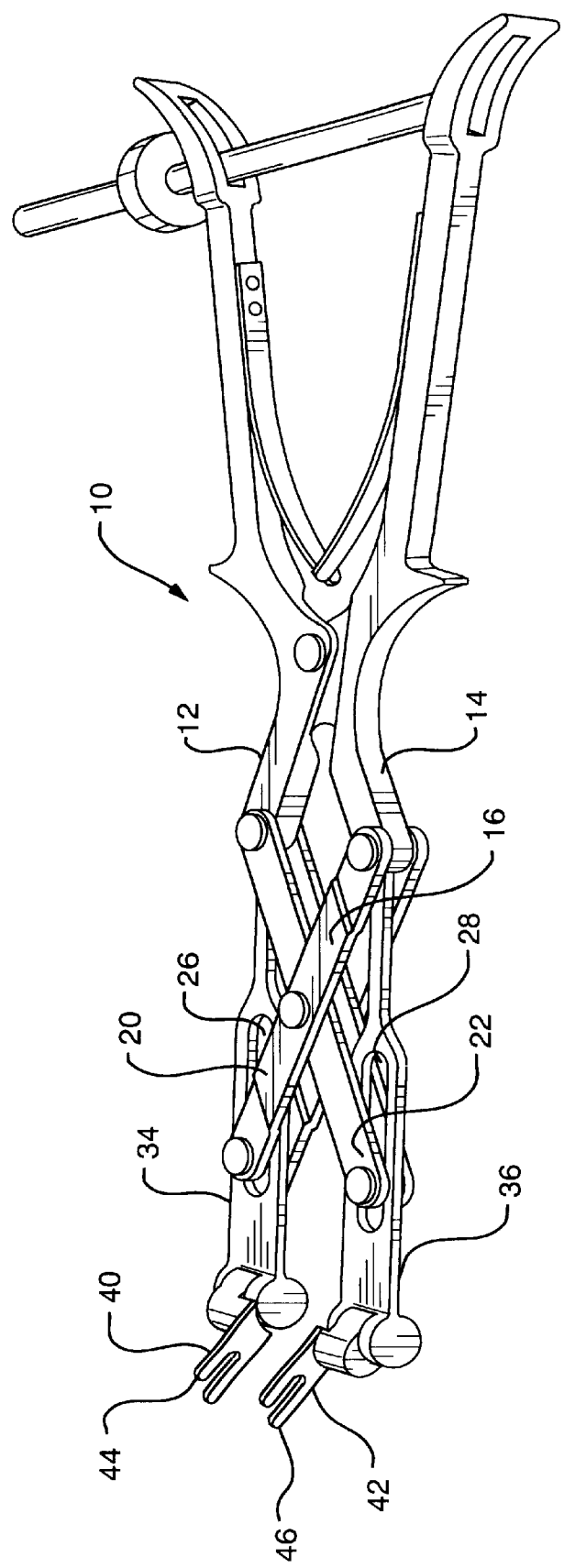
FIG. 1 is an isometric view of a bone distractor instrument including the ratcheting tips of the present invention.

FIG. 1 illustrates an instrument 10 for bone distraction and compression. The instrument 10 has handles, which include first handle member 12 and an opposed, second handle member 14. Handle members 12 and 14 are interconnected by slot and pin assembly 16.

Figure 2:
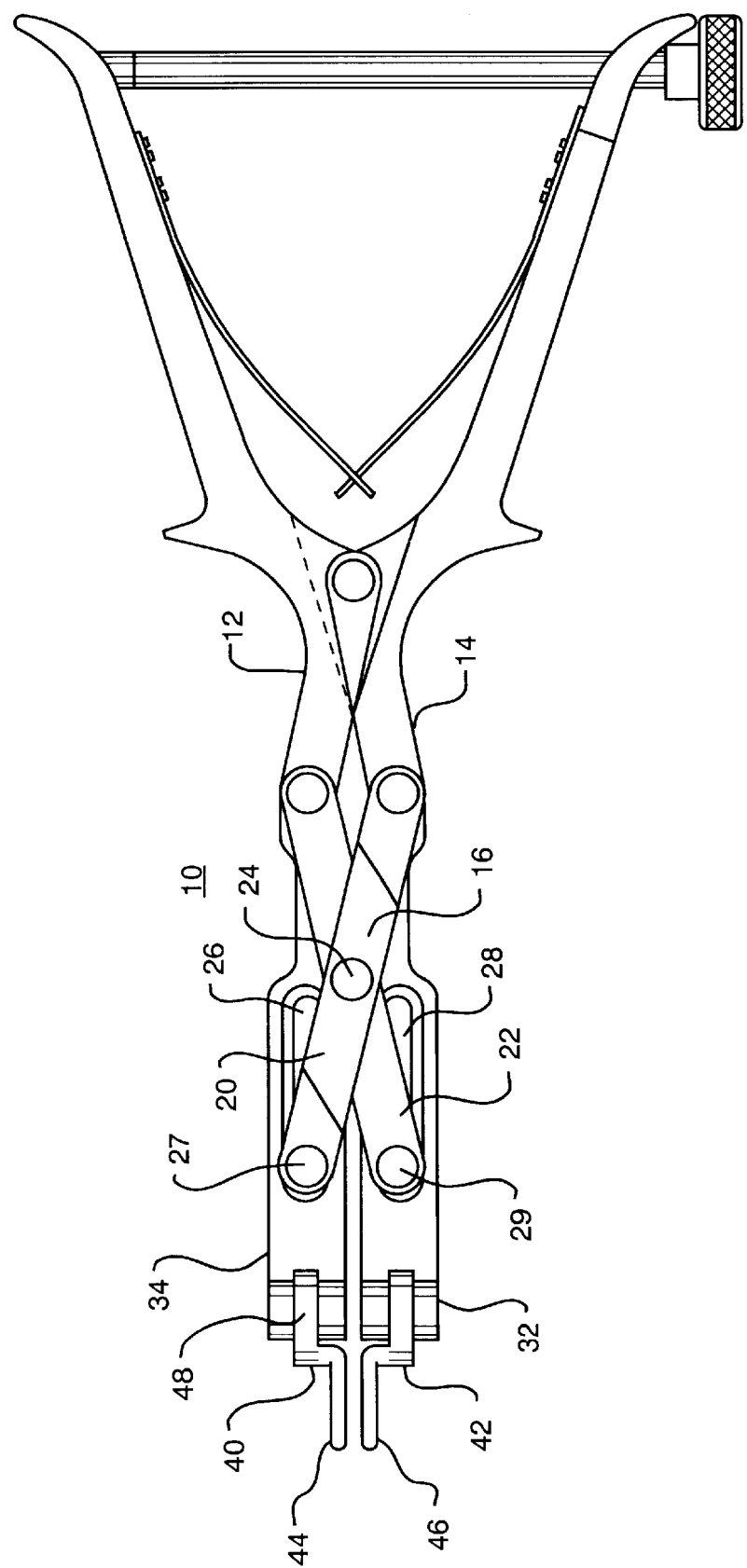
FIG. 2 is a top plan view of the bone distractor of the present invention.

As illustrated in FIG. 2, slot and pin assembly 16 includes upper bar 20 and a lower bar 22 which are interconnected at a center pin 24. Upper bar 20, for example, slides along the slot 26 via pin 27. Similarly, lower bar 22 slides along slot 28 via pin 29, when handle members 12 and 14 are manipulated. This allows for a parallel opening at ends 30, 32 of the instrument 10. This is in contrast to the typical instrument that, when opened, exhibits an arc-shaped pattern. When opened and closed, the ends 30, 32 of the instrument 10 illustrated in FIG. 2, remain parallel to one another.

Figure 3:
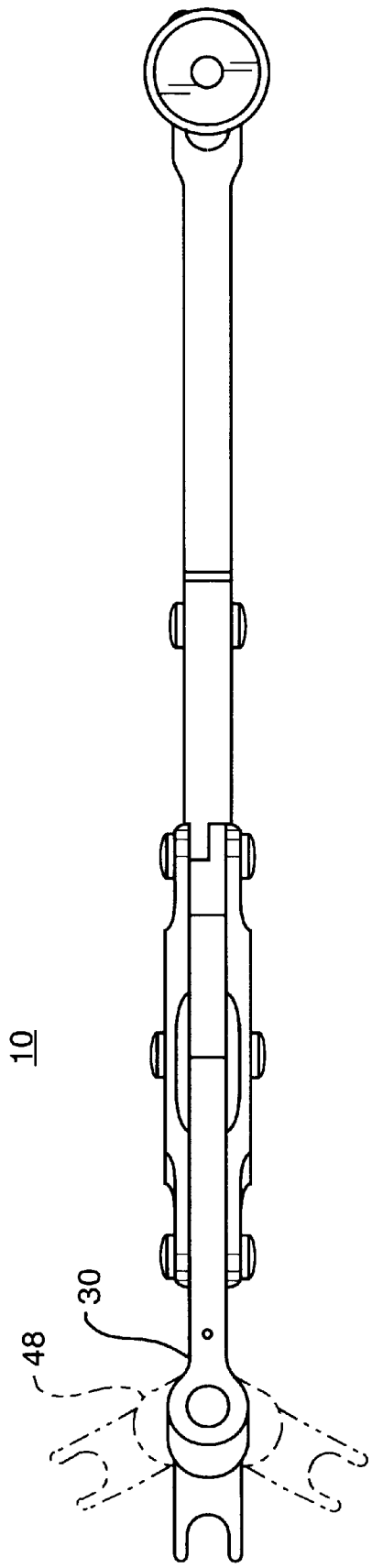
FIG. 3 is a side section of the bone distractor of FIG. 2.
Figure 5:
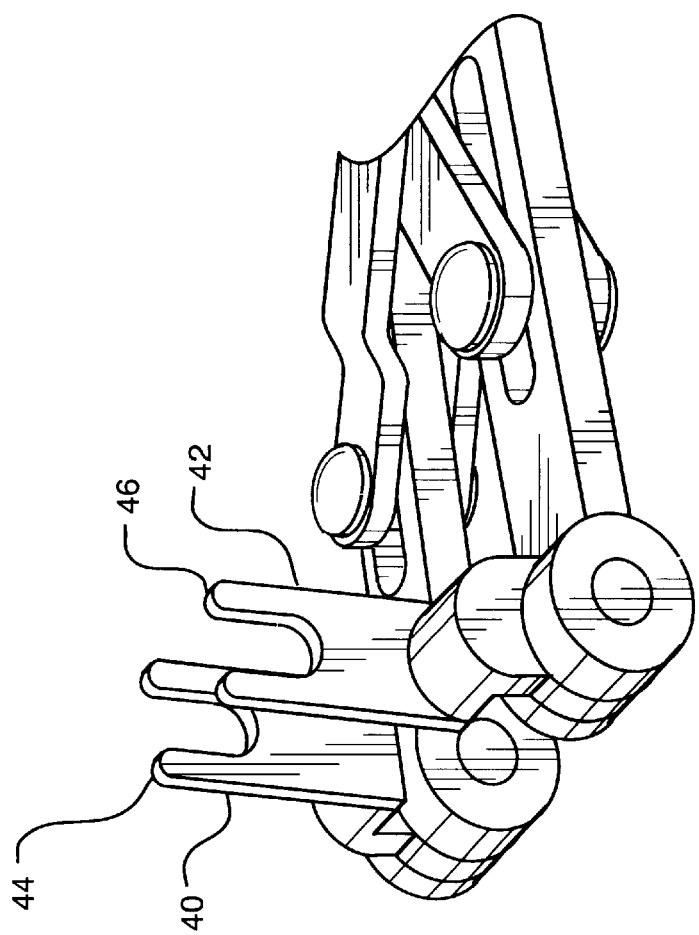
FIG. 5 is another isometric view from one side of the ratcheting tips on the bone distractor of the present invention.

The end 30 of the handle member 12 has a shaft 34 upon which a tip 40 is rotatably mounted. In the embodiment illustrated in the Figures, the tip 40 includes a U-shaped end 44, which engages the rod hook or implant with which the surgeon is working during a procedure. If the instrument to be applied to bone, a different tip is used that has an appropriate configuration, instead of a U-shape. The rotatable tip 40 also includes a wheel member 48 (FIG. 3). The wheel member 48 is rotatable about an imaginary Z-axis that is perpendicular to the plane of the figure.

Figure 4:
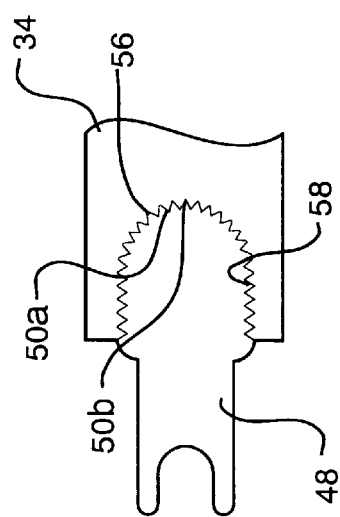
FIG. 4 is an exploded side section of one end of the bone distractor instrument of the present invention illustrating the ratcheting tips in further detail.

As illustrated in FIG. 4, the wheel member 48 has a set of ratcheting teeth, such as the teeth 50a, 50b. The end 30

(shown in cutaway in FIG. 4) includes a pawl 56, which is formed in the recess 58 of the shaft 34 of the handle member 12. A similar assembly is provided with respect to the opposed shaft 36 of member 14, but only one is shown for clarity of illustration. The pawl 56 engages one of the teeth 50a to hold the tip 40 in the selected position.

In operation, the tips 40, 42 are rotated by the surgeon prior to surgery until the ratcheting teeth 50a, 50b are engaged by the pawl 56 at the angle at which the surgeon prefers to work in the particular application. This is most likely an angle that provides the best visualization for the surgeon, while still allowing the surgeon the leverage to maintain pressure to accomplish the desired distraction or compression for that particular procedure. The surgeon then places the U-shaped openings 44 and 46 of the handle members 12 and 14 around the rod hook to be distracted or compressed, and applies the appropriate pressure. The ratcheting tips 40, 42 may be later adjusted, if desired.

In accordance with another aspect of invention, the tips can be mounted such that they can be adjusted into any position and then locked into place relative to the shaft within an appropriate fastening member. It should be understood that the instrument of the present invention allows the surgeon the best visualization while maintaining the leverage needed to accomplish the desired task or to apply pressure or force to the area to be manipulated during surgery.

The foregoing description has been directed to specific embodiments of the invention. It will be apparent however that other variations and modifications may be made to the described embodiments with the attainment of some or all of the advantages of such, therefore, it is the object of the appended claims to cover all such variations and modifications as come within the true spirit and scope of the invention.

What is claimed is:

1. A surgical instrument for distraction and compression, comprising:
    an instrument body having at least two members, each said member having a handle portion at one end, and a working portion at an opposite end being the working end;
    a connection assembly coupling together said two members, and which connection assembly allows for a parallel opening at the working ends of each member; and
    a distraction and compression tip being disposed at each said working end of each said member for engaging an object to be manipulated during a surgical procedure and wherein each said member includes a ratcheting mechanism that allows the tip at said working end of each said member to be adjusted angularly for a particular surgical procedure.

2. The instrument as described in claim 1 wherein at least one of said distraction and compression tip of said working end has a U-shape, for engaging an object to be manipulated during a surgical procedure.

3. The surgical instrument as defined in claim 2 wherein said U-shaped distraction and compression tip is sized to engage a stabilization rod implanted in proximity to the spine of a patient having said surgical procedure.

4. The surgical instrument as defined in claim 2 wherein said U-shaped distraction and compression tip is sized to engage rod hooks of a stabilization rod used in a surgical procedure.

5. The instrument as defined in claim 1 wherein at least one of said distraction and compression tip at the working end of each member is detachable.

6. The surgical instrument as defined in claim 1 wherein said distraction and compression tip of said surgical instrument is sized to engage and push an implant along a surgical implantation rod.

7. The surgical instrument as defined in claim 1 wherein said ratcheting mechanism includes a rotatable wheel member that has a set of ratcheting teeth, and said handle member of said instrument body having a shaft with a recess formed in one end thereof that includes a pawl that engages one of the ratcheting teeth in said wheel member to hold the tip in a stationary position.

8. The surgical instrument as defined in claim 7 wherein said connection assembly coupling together said two members is a slot and pin assembly disposed along the shafts of said members.

9. A surgical instrument for distraction and compression, comprising:
    an instrument body having at least two members, each said member having a handle portion at one end, and a working portion at an opposite end being the working end;
    a connection assembly coupling together said two members; and which connection assembly allows for a parallel opening at the working ends of each member; and
    a distraction and compression tip being disposed at each said working end of each said member for engaging an object to be manipulated during a surgical procedure and wherein each said member of said instrument body includes a shaft in which said tip is rotatably mounted.

10. The surgical instrument as defined in claim 9 wherein said tip is rotatably mounted on said shaft in such a manner that it can be rotatably adjusted at 15° intervals.

11. The surgical instrument as defined in claim 9 further comprising a fastening member for securing said tips as adjusted into a particular predetermined position and locking said tips into place relative to said shaft, whereby a surgeon performing said surgical procedure is allowed improved visualization while leverage is maintained to apply desired pressure or force to the area being manipulated during surgery.

* * * * *